(12) United States Patent
Goodwin, III et al.

(10) Patent No.: US 6,281,388 B1
(45) Date of Patent: Aug. 28, 2001

(54) LOW PRESSURE AMINE REACTOR

(75) Inventors: Ralph T. Goodwin, III, Cantonment; Gregory J. Ward, Gulf Breeze, both of FL (US)

(73) Assignee: Solutia Inc., St. Louis, MO (US)

(*) Notice: Subject to any disclaimer, the term of this patent is extended or adjusted under 35 U.S.C. 154(b) by 0 days.

(21) Appl. No.: 09/460,051

(22) Filed: Dec. 13, 1999

Related U.S. Application Data

(60) Provisional application No. 60/113,329, filed on Dec. 22, 1998.

(51) Int. Cl.⁷ .................................................. C07C 209/48

(52) U.S. Cl. ............................................................ 564/492

(58) Field of Search ............................................. 564/492

(56) References Cited

U.S. PATENT DOCUMENTS 3,821,305 * 6/1974 Bartalini et al. ..................... 564/492

* cited by examiner

*Primary Examiner*—Johann Richter
*Assistant Examiner*—Brian J. Davis
(74) *Attorney, Agent, or Firm*—Howrey Simon Arnold & White, LLP

(57) ABSTRACT

A method for the production of an amine from a nitrile utilizing hydrogenation by; feeding hydrogen and nitrile into a reactor including catalyst, water and inorganic base to form a reaction medium; mixing the reaction medium to provide a uniform bulk concentration of the nitrile in at least one direction across the reactor to minimize the reactor volume where local bulk nitrile concentration exceeds that stoichiometrically required to completely deplete the local bulk hydrogen concentration; and hydrogenating the nitrile to form the amine.

21 Claims, 1 Drawing Sheet

LOW PRESSURE AMINE REACTOR

This application claims the benefit of U.S. provisional application Ser. No. 60/113,329, filed Dec. 22, 1998.

FIELD OF THE INVENTION

The invention relates to a process for the production of an amine from a nitrile, where the reaction is conducted in the presence of a catalyst. The invention also relates to a reactor for producing an amine from a nitrile.

BACKGROUND OF THE INVENTION

It is well known that amines such as hexamethylene diamine, propyl amines, butyl amines, benzyl amines, tallow amines, ethyl amines, etc., may be produced by the catalytic hydrogenation of nitriles such as proprionitrile, butyronitriles, tallow nitriles, acetonitriles, etc., in the presence of catalysts and other substances such as ammonia and/or caustic alkali. As set forth in U.S. Pat. No. 3,821,305, the entire subject matter of which is incorporated herein by reference, one such process is described in which hydrogenation is conducted in liquid phase at pressures of from 20–50 atmospheres and temperatures of 60°–100° C. in the presence of finely divided Raney catalyst and an inorganic base. Hydrogen and adiponitrile are fed into a liquid reaction medium consisting of hexamethylenediamine, water, the inorganic base, and the catalyst, in which medium the content of base is maintained in the range of 0.2–12 moles per kilogram of catalyst, while the content of water is maintained in the range of 2–130 moles per mole of the base.

In typical continuous processes utilizing a Raney nickel or Raney cobalt hydrogenation catalyst, the rate at which the catalyst is fed into the reaction medium must be carefully controlled. Active catalysts of that type are pyrophoric, however, and are therefore normally kept out of contact with air by transporting and storing the catalyst in a relatively inert liquid. Hence, in some of the aforementioned processes, the rate at which the catalyst is fed into the reaction medium is desirably controlled by suspending the catalyst in such a liquid so as to disperse the catalyst substantially uniformly through the liquid in a known concentration of catalyst per unit volume of the suspension, and then controlling the volumetric flow rate of the suspension into the reaction mixture. Examples of processes in which the catalyst feed rate may be conveniently controlled in this way are described in U.S. Pat. No. 3,821,305, the disclosure of which is incorporated herein by reference, and in U.S. Pat. No. 3,056,837, the disclosure of which also is incorporated herein by reference.

However, Raney nickel and cobalt catalysts in such processes have been plagued by high deactivation rates under certain conditions when utilized in the hydrogenation of nitrites. For example, an article in Chemical Engineering Science, Vol. 47, No. 9–11, 2289–94 (1992), indicates that nitrites deactivate nickel or cobalt catalysts, such as Raney nickel catalysts. More recently, efforts have been made to reduce such catalyst deactivation rates. For example, it is also known in such low pressure hydrogenation systems to utilize high liquid recirculation velocities in an attempt to provide good mixing conditions found in turbulent flow so as to enhance catalyst stability and increase mass transfer coefficients as set forth in Chemical Engineering Science, Vol. 35, 135–141 (1980).

Additionally, efforts have been made to study reactors to determine the effect of operating conditions on catalyst deactivation rates. For example, in Catalysis Today, 24, 103–109 (1995) catalyst deactivation effects under various operating conditions for hydrogenation of adiponitrile, in a continuous bench scale slurry bubble column reactor were investigated. The reactor was considered to be mixed perfectly because the temperatures at the top and bottom of the column were identical and the differences in concentration between the samples taken at the top and the bottom of the column were less than 15%.

Efforts have also been made to reduce catalyst deactivation by physically blocking the active catalyst sites or access to the sites and equipment fouling in hydrogenation reactions by increasing mass transfer rates in the reactor system, i.e., see "Pumped-up Mixer Improves Hydrogenation," Chemical Engineering, June 1998, p. 19, in which increased mass transfer rates reduced catalyst physical deactivation and equipment fouling in hydrogenation reactions for the production of edible oils. However, the local bulk concentrations of reactants in such reactors varies considerably and will not inhibit chemical catalyst deactivation (i.e., catalyst deactivation by irreversibly depleting the catalyst of elements (e.g., interstitial hydrogen)) necessary for adequate catalyst activity in nitrile hydrogenation reactions.

However, it has now been discovered that contrary to the assumptions and inferences made in the above-mentioned prior reactor configurations for the hydrogenation of nitrites, the reactants in such reactors are not perfectly mixed across the diameter of the reactor. According to the present invention, studies have been made that indicate the local bulk nitrile concentration in such reactors is not uniform and through most of the reactor the local bulk nitrile concentration exceeds that stoichiometrically required to completely deplete the local bulk hydrogen concentration, which leads to an increased catalyst chemical deactivation rate. Accordingly, there is a need to provide certain reactor conditions that would provide reduced chemical catalyst deactivation rates in nitrile hydrogenation systems.

SUMMARY OF THE INVENTION

The present invention relates to a method for the production of an amine from a nitrile by hydrogenation comprising; feeding hydrogen and nitrile into a reactor comprising catalyst, water and inorganic base to form a reaction medium; mixing the reaction medium to provide a uniform local bulk concentration of the nitrile in the reactor; and hydrogenating the nitrile to form the amine. Moreover, the present invention relates to a method for the production of an amine from a nitrile by hydrogenation while minimizing the reactor volume where local bulk nitrile concentrations exceed that stoichiometrically required to completely deplete the local bulk hydrogen concentration.

DETAILED DESCRIPTION OF PREFERRED EMBODIMENTS

Figure 1:
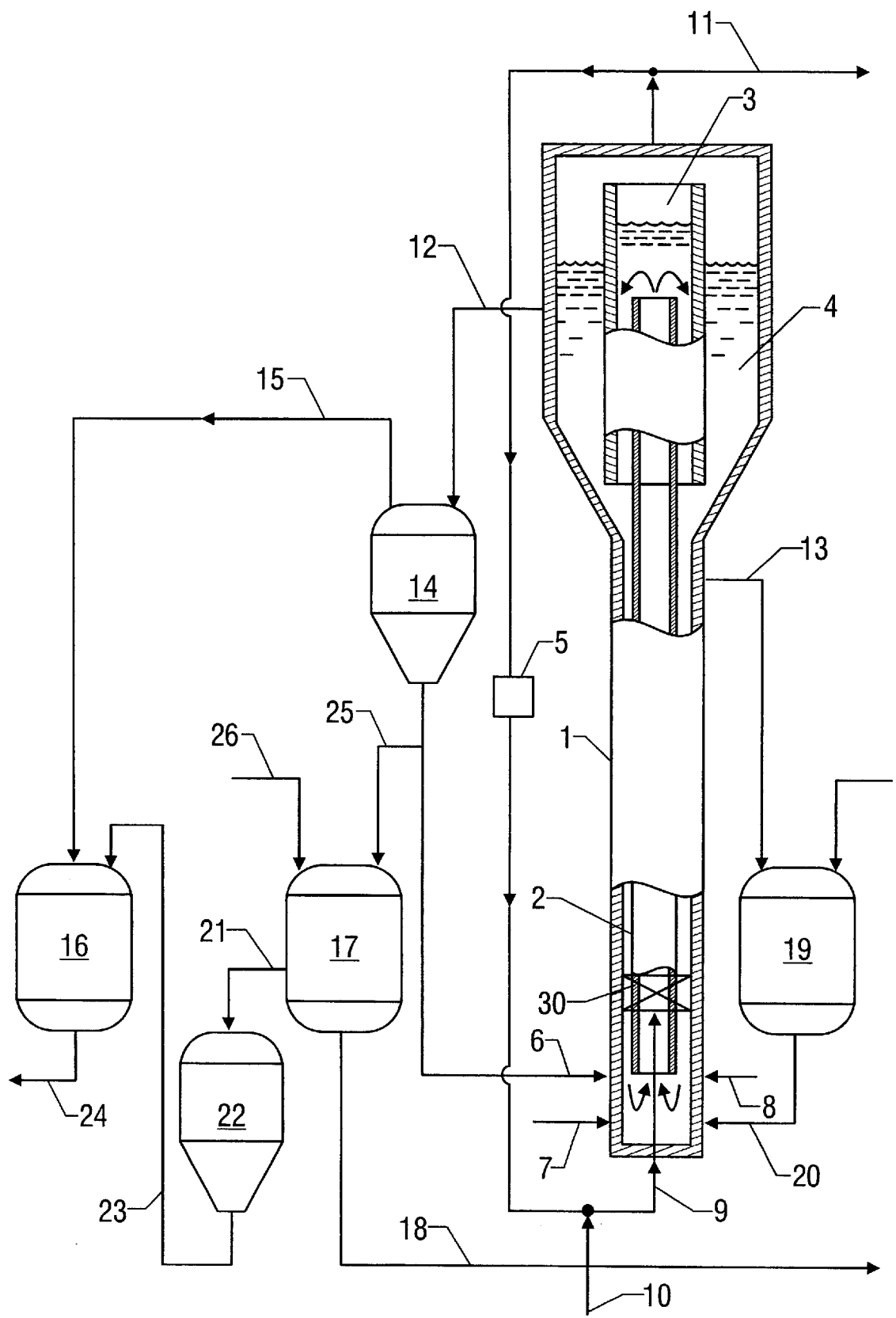
FIG. 1 is a schematic illustration of a reactor suitable for practicing the invention.

While the invention is applicable to the process for the production of any amine including aliphatic and aromatic amines and their derivatives, such as hexamethylene diamine, propyl amines, butyl amines, benzyl amines, tallow amines, ethyl amines, etc., produced from a nitrile including aliphatic and aromatic nitrites and their derivatives such as proprionitrile, butyronitriles, tallow nitrites, acetonitriles, benzyl nitrites, etc., in which finely divided catalyst is suspended in the liquid reaction medium, the invention will be described in the context of a preferred process for such production.

For example, a process for an amine may be carried out at pressures of 20–50 atmospheres and at temperatures of 60° to 120° C., by feeding hydrogen and nitrile into a liquid reaction medium containing, along with the amine produced, water, inorganic base and a finely divided nickel or cobalt catalyst dispersed in the liquid components of the reaction medium. The catalyst, which preferably is Raney nickel, with or without promotor metals such as chromium and/or iron, loses all or most of its activity during hydrogenation.

To maintain a given level of catalytic activity within the catalytic mass, it is necessary for the catalyst in the reaction medium to be gradually replaced. This replacement is effected by feeding fresh catalyst to the reaction vessel and removing a quantity of reaction medium which contains an amount of catalyst equal to that supplied. The feed catalyst may consist of a mixture of fresh catalyst and of recycled catalyst. Recycled catalyst is catalyst that has been washed prior to re-use.

The reaction medium preferably contains:

(1) a quantity of catalyst in excess of 1 part, by weight, per 100 parts of liquid reaction medium (amine, water and inorganic base), the upper limit depending solely on the fluidity of the reaction medium; the preferred range is from 3 to 35 parts per 100 parts by weight of the liquid reaction medium;

(2) a quantity of inorganic base in the range of 0.2 to 12 moles per kilogram of catalyst and preferably between 1 and 3 moles per kilogram of catalyst;

(3) a quantity of water in the range of 2 to 130 moles per mole of inorganic base and preferably between 7 and 70 moles per mole of inorganic base.

Preferably, the inorganic base comprises alkali metal hydroxide, such as sodium, potassium, lithium, rubidium, or cesium. More preferably, the inorganic base comprises a mixture of two or more alkali metal hydroxides. For example, synergistic results (e.g., improved catalyst stability and improved selectivity for the primary amine) have been obtained using a mixture of sodium hydroxide and potassium hydroxide.

The liquid part of the reaction medium, under the starting conditions already specified, and within the preferred range of ratio of water to inorganic base, consists of an aqueous solution of inorganic base whose concentration is in the range of 25 to 70%, preferably 30 to 60%, and, more preferably 40 to 50% by weight of the aqueous solution. The other phase consists of amine containing water and small amounts of inorganic base. The aqueous solution of inorganic base, which is the heavier phase, contains most of the catalyst.

In accordance with the present invention, so as to reduce the chemical catalyst deactivation rate, it has been discovered that the local bulk concentration of nitrile be uniform in at least one direction across the reactor with substantially the same extent of reaction. Moreover, in accordance with the present invention, chemical catalyst deactivation may be minimized by maintaining conditions such that the local bulk nitrile concentration is less than that stoichiometrically required to completely deplete the local bulk hydrogen concentration in the reactor; for example, one mole per liter of adiponitrile is stoichiometrically required to completely deplete 4 moles per liter of hydrogen ($H_2$) to produce to one mole per liter of hexamethylenediamine. As defined herein, "chemical" catalyst deactivation refers to the reduction in activity of the catalyst by altering the chemical composition of the catalyst, "physical" catalyst deactivation refers to the reduction in activity of the catalyst by limiting the accessible number of active sites of the catalyst, such as by blocking the pores of the catalyst (e.g., coking), and local bulk concentration refers to the average concentration of a chemical species in a sample volume centered on a catalyst particle with the sample volume having a diameter between about 100 times the catalyst particle diameter and about 0.1 times the characteristic length scale of the reactor, e.g. the reactor diameter in a tubular reactor. In the present invention, 'local bulk' nitrile concentration gradients refers to gradients in nitrile concentration over length scales of the order of magnitude of the dimensions of the reactor rather than gradients in nitrile concentration over length scales with dimensions of the order of magnitude of the catalyst particles.

For example, in a tubular reactor, the extent of reaction is substantially constant in a plane perpendicular to the axis of the tube, while in a stirred tank reactor the extent of reaction is substantially the same at all points in the reactor. As above-mentioned, chemical catalyst deactivation rates are higher in reactor zones where the local bulk nitrile concentration exceeds that stoichiometrically required to completely deplete the local bulk hydrogen concentration and where such local bulk nitrile concentration comes into contact with the catalyst. Accordingly, the present invention reduces the rate of chemical catalyst deactivation by substantially eliminating local bulk concentration gradients through zones in the reactor with substantially the same extent of reaction while also minimizing the volume of the reactor where local bulk nitrile concentration exceeds that stoichiometrically required to completely deplete the local bulk hydrogen concentration.

Generally, within a zone of constant extent of reaction, the coefficient of variation of bulk nitrile concentration (100 times standard deviation divided by mean) is less than 250%, preferably less than 150%, and even more preferably less than 100%. Generally, the conditions in the reactor are maintained such that the local bulk concentration of nitrile is less than the local bulk concentration of hydrogen throughout greater than about 30% of the volume of the reactor, preferably greater than about 40%, and more preferably greater than about 50%.

In an embodiment of the present invention, the nitrile hydrogenation process may be performed in tubular reactors, such as gas lift reactors.

An example of such a reactor, which is not limitive of the invention, is shown in the accompanying drawing (FIG. 1).

The equipment for continuous operation of the process is of conventional type. An example of this, which is not limitive of the invention, is shown in the accompanying drawing. The equipment consists essentially of a vertical tubular reaction vessel 1 provided inside with an injection device 2, such as to promote the agitation of the reaction medium resulting from the hydrogen flow 9, mixing device 30, and at the top with containers 3 and 4, which enable the separation of the gas from the liquid and the drawing off from the reaction vessel of a hydrogenated product having a low content of catalyst thus making it possible to maintain in the reaction vessel relatively high concentration of catalyst—for example, 10 to 30 parts of catalyst per 100 parts by weight of liquid reaction medium.

The equipment also includes a gas re-cycling pump 5 and pipes for feeding the reaction vessel with adiponitrile 8, aqueous caustic solution 7, and hydrogen 9. The hydrogen consumed is replaced by feeding fresh hydrogen through pipe 10.

Part of the gas is vented through pipe 11, the purpose of this release being to maintain the hydrogen content in the re-cycled gas above a given value.

Product stream 12 from the reactor is discharged into decanter 14 where the upper layer containing crude hexamethylene diamine is discharged through pipe 15 and on to settling tank 16, thence through pipe 24 to further purification measures including distillation. The lower layer of the decanter, 14, is separated into two portions, the first going to pipe 6 which is returned to the reactor and the second going to pipe 25 which discharges into wash tank 17. Wash tank 17 is fed by pipe 26 containing water, and the washed catalyst is returned to the reactor via catalyst tank 19 and pipe 20. The catalyst wash water is discharged from tank 17 into hold tank 22 via pipe 21, thence through pipe 23 to pipe 16.

In tubular reactors, the flow rate of the reaction medium for hydrogenation of nitrites is quite high (i.e., turbulent flow with Reynolds numbers above 2000). Even with turbulent flow, which would have been expected to provide sufficient mixing of the reaction medium, nonuniform local bulk concentration in these reactors exists. Additional mixing mechanisms must be utilized to provide the uniform local bulk nitrile concentration of the present invention. Such additional mixing may be provided by static mixers, mechanical mixers, jet mixers or by reactor design. In tubular reactors, the mixing is provided preferably by static mixers.

For example, the mixing device 30 may be a static mixer, such as a low pressure drop vortex mixer, an orifice mixer, a mixing nozzle, valves, a pump, an agitated line mixer, packed tubes, or a long pipe line. Additionally, the mixing device 30 may be a mechanical mixer, such as an impeller, a pump, or the like; or the mixing device 30 may be a jet mixer. Preferably, the mixing device is a static mixer, more preferably, a low pressure drop vortex mixer. The mixing device may be placed at various locations in the reactor. However, in order to be more effective in providing uniform local bulk nitrile concentration, the mixer is placed in the reactor vessel in close proximity to the nitrile feed stream.

The uniform bulk nitrile concentration may be implemented with other reactor configurations, such as stirred tank reactors, bubble column reactors, or the like. Such mixing conditions may be implemented as mentioned herein.

EXAMPLES

The mixing may be characterized by flow visualization experiments involving, for example, injection of a dye into a scaled or full-scale transparent mock-up of the reactor, or may be caluclated using computational fluid dynamics. In the present examples, a gas lift reactor, as illustrated in the FIGURE, is utilized to prepare hexamethylene diamine from adiponitrile and hydrogen with a Raney nickel catalyst.

Flow condition are maintained such that the Reynolds number of the reaction mass was about 1.6 million.

The following table indicates the coefficient of variation in total nitrile concentration as a function of position in the reactor, with and without a mixer. The mixer utilized in these examples is a static mixer, particularly a low pressure drop vortex mixer. The mixer is placed directly above the adiponitrile feed stream in the reactor.

| Position (% of reactor length) | No Mixer | With Mixer |
|---|---|---|
| 0 | 738 | 739 |
| 10 | 312 | 87 |

-continued

| Position (% of reactor length) | No Mixer | With Mixer |
|---|---|---|
| 20 | 253 | 28 |
| 30 | 217 | 16 |
| 40 | 189 | 11 |
| 50 | 161 | 6 |
| 60 | 139 | 6 |
| 70 | 112 | 6 |
| 80 | 97 | 6 |
| 90 | 80 | 6 |
| 100 | 62 | 5 |

Without the mixer, the mean variance in total nitrile concentration is 185%. With a static mixer, the mean variance in total nitrile concentration is reduced to 39%.

Without the mixer, the local bulk nitrile concentration exceeds that stoichiometrically required to completely deplete the local bulk hydrogen concentration in about 8% of the volume of the reactor after the adiponitrile sparger. With a static mixer, the local bulk nitrile concentration exceeds that stoichiometrically required to completely deplete the local bulk hydrogen concentration in less than 1% of the volume of the reactor after the adiponitrile sparger.

What is claimed is:

1. A method for the production of an amine from a nitrile by hydrogenation comprising;

feeding hydrogen and nitrile into a reactor comprising catalyst, water and inorganic base to form a reaction medium;

mixing said reaction medium to provide a uniform local bulk concentration of said nitrile in at least one direction across said reactor; and hydrogenating said nitrile to form said amine.

2. A method according to claim 1, wherein said nitrile is adiponitrile and said amine is hexamethylene diamine.

3. A method according to claim 1, wherein said inorganic base comprises an alkali metal hydroxide.

4. A method according to claim 1, wherein said inorganic base comprises lithium hydroxide, sodium hydroxide, potassium hydroxide, rubidium hydroxide, or cesium hydroxide.

5. A method according to claim 1, wherein said inorganic base is a mixture of sodium hydroxide and potassium hydroxide.

6. A method according to claim 1, wherein the catalyst is a Raney nickel catalyst in the form of finely divided particles.

7. A method according to claim 1, wherein said reactor comprises a stirred tank reactor, a gas lift reactor, a tubular reactor, or a bubble column reactor.

8. A method according to claim 1, wherein said reactor is a gas lift reactor.

9. A method according to claim 1, wherein said mixing comprises static mixing, mechanical mixing or jet mixing.

10. A method according to claim 1, wherein said mixing provides turbulent flow of said reaction medium having a Reynolds Number of at least 2000.

11. A method according to claim 1, wherein hydrogenating is conducted at pressures of 20 to 50 atmospheres and temperatures of 60° to 120° C.

12. A method according to claim 1, wherein within zones of substantially uniform extent of reaction, the coefficient of variation of bulk nitrile concentration in at least one direction across the reactor is less than 250%.

13. A method according to claim 1, wherein within zones of substantially uniform extent of reaction, the coefficient of variation of bulk nitrile concentration in at least one direction across the reactor is less than 150%.

14. A method according to claim 1, wherein within zones of substantially uniform extent of reaction, the coefficient of variation of bulk nitrile concentration in at least one direction across the reactor is less than 100%.

15. A method according to claim 1, wherein the local bulk nitrile concentration is less than that stoichiometrically required to completely deplete the local bulk hydrogen concentration in more than 92% of the volume of the reactor.

16. A method according to claim 1, wherein the local bulk nitrile concentration is less than that stoichiometrically required to completely deplete the local bulk hydrogen concentration in more than 95% of the volume of the reactor.

17. A method according to claim 1, wherein the local bulk nitrile concentration is less than that stoichiometrically required to completely deplete the local bulk hydrogen concentration in more than 99% of the volume of the reactor.

18. A method for the production of an amine from a nitrile by hydrogenation comprising;

feeding hydrogen and nitrile into a reactor comprising catalyst, water and inorganic base to form a reaction medium;

mixing said reaction medium to minimize regions having a local bulk concentration of said nitrile greater than the local bulk concentration of said hydrogen throughout the volume of said reactor; and hydrogenating said nitrile to form said amine.

19. A method according to claim 18, wherein the local bulk nitrile concentration is less than that stoichiometrically required to completely deplete the local bulk hydrogen concentration in more than 92% of the volume of the reactor.

20. A method according to claim 18, wherein the local bulk nitrile concentration is less than that stoichiometrically required to completely deplete the local bulk hydrogen concentration in more than 95% of the volume of the reactor.

21. A method according to claim 18, wherein the local bulk nitrile concentration is less than that stoichiometrically required to completely deplete the local bulk hydrogen concentration in more than 99% of the volume of the reactor.

* * * * *